(12) United States Patent
Myers et al.

(10) Patent No.: US 12,150,917 B2
(45) Date of Patent: Nov. 26, 2024

(54) MEDICATION CHANGE SYSTEM AND METHODS

(71) Applicant: Express Scripts Strategic Development, Inc., St. Louis, MO (US)

(72) Inventors: Christopher M. Myers, Dublin, OH (US); Danielle L. Smith, Cedar Park, TX (US); Daniel McConnell, Rolla, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 357 days.

(21) Appl. No.: 17/586,460

(22) Filed: Jan. 27, 2022

(65) Prior Publication Data

US 2023/0233414 A1 Jul. 27, 2023

(51) Int. Cl.
 *A61J 7/00* (2006.01)
 *G06V 10/22* (2022.01)
 (Continued)

(52) U.S. Cl.
 CPC .......... *A61J 7/0084* (2013.01); *G06V 10/235* (2022.01); *G06V 10/56* (2022.01); *G06V 10/82* (2022.01);
 (Continued)

(58) Field of Classification Search
 CPC .. A61J 7/0084; A61J 2205/20; A61J 2205/40; G16H 20/10; G06V 10/56; G06V 10/235; G06V 10/82
 (Continued)

(56) References Cited

U.S. PATENT DOCUMENTS 6,535,637 B1 * 3/2003 Wootton ................. B65B 57/00
 221/102
8,712,163 B1 * 4/2014 Osheroff ............ G06Q 30/0185
 424/467
(Continued)

FOREIGN PATENT DOCUMENTS

| AU | 2017252847 A1 * | 11/2018 | ................ A61J 3/00 |
| WO | WO-2015060296 A1 * | 4/2015 | ............ G16H 70/40 |
| WO | WO-2018078613 A1 * | 5/2018 | ........... B07C 5/3422 |

OTHER PUBLICATIONS

Hartl, Andreas. "Computer-vision based pharmaceutical pill recognition on mobile phones." Proc. 14th Central European Seminar on Computer Graphics. 2010.
(Continued)

*Primary Examiner* — Rakesh Kumar
(74) *Attorney, Agent, or Firm* — Schwegman Lundberg & Woessner, P.A.

(57) ABSTRACT

Method for generating user interface that indicates medication changes in medication starts with a processor detecting a medication change event. Processor retrieves medication information based on the medication change event including images of two medications. Processor generates color difference output using a color neural network, image of first medication and second medication. Color difference output comprises information on a difference in hue, saturation or color distribution. Processor generates medication appearance difference output using medication appearance neural network, image of first medication and second medication. Medication appearance difference output comprises information on a difference in shape, segmentation or form. Processor generates a differential record using the color difference output and medication appearance difference output. Processor causes medication change user interface to be displayed that comprises medication images and color and
(Continued)

appearance descriptions of the medication which are displayed to emphasize differences identified in the differential record. Other embodiments are disclosed herein.

20 Claims, 12 Drawing Sheets
(3 of 12 Drawing Sheet(s) Filed in Color)

(51) Int. Cl.
    *G06V 10/56*     (2022.01)
    *G06V 10/82*     (2022.01)
    *G16H 20/10*     (2018.01)

(52) U.S. Cl.
    CPC .......... *G16H 20/10* (2018.01); *A61J 2205/20* (2013.01); *A61J 2205/40* (2013.01)

(58) Field of Classification Search
    USPC .......................................................... 221/2
    See application file for complete search history.

(56) References Cited

U.S. PATENT DOCUMENTS

| | | | |
|---|---|---|---|
| 8,727,208 B2* | 5/2014 | Poisner | G01N 21/9508 235/494 |
| 9,076,107 B2* | 7/2015 | Cameron | G16H 50/20 |
| 9,098,900 B2* | 8/2015 | Helgason | G06V 10/145 |
| 9,251,493 B2* | 2/2016 | Jacobs | H04N 23/90 |
| 9,253,370 B2* | 2/2016 | Komatsubara | G01J 3/463 |
| 10,368,770 B2 | 8/2019 | Lithgow | |
| 10,546,235 B2* | 1/2020 | Moudy | H04L 67/01 |
| 10,552,575 B1* | 2/2020 | Mohebbi | G06F 18/22 |
| 10,565,545 B2* | 2/2020 | Yonaha | G06Q 10/087 |
| 10,713,540 B2 | 7/2020 | Zhang | |
| 2010/0324936 A1 | 12/2010 | Vishnubhatla et al. | |
| 2014/0355849 A1 | 12/2014 | Brossette | |
| 2014/0365242 A1 | 12/2014 | Neff | |
| 2017/0161469 A1 | 6/2017 | Shibahara | |
| 2018/0294059 A1 | 10/2018 | Savant | |
| 2019/0139636 A1 | 5/2019 | Chandrasekaran | |
| 2020/0082923 A1 | 3/2020 | Harrison | |
| 2021/0074421 A1 | 3/2021 | Gopalakrishnan | |
| 2023/0233414 A1* | 7/2023 | Myers | G06V 10/56 221/2 |

OTHER PUBLICATIONS

Lee, et al. "Pill-id: Matching and retrieval of drug pill imprint images." 2010 20th International Conference on Pattern Recognition. IEEE, 2010.

* cited by examiner

MEDICATION CHANGE SYSTEM AND METHODS

BACKGROUND

Since a user's perception of an organization can be greatly influenced by the customer service that is provided to the user, the organization has interest in ensuring that the user's experience with the customer service is impeccable. While, traditionally, customer service is a face-to-face interaction between the user and an agent that is employed by the organization, in order to increase the ability for the user to access to an agent of the organization, customer service is now accessible via many different means of communication. For example, a user may communicate with a human agent or an automated agent via an audio call (e.g., voice over IP (VoIP), telephone) or via an electronic messaging (e.g., online chat, text messaging).

Whether the user is interacting with a human agent or an automated agent, customer service aims to help the user complete his transaction in the most timely and efficient manner while ensuring that the user's experience with the customer service is enjoyable. A user's experience is also further optimized when the user's needs or questions for customer service are anticipated such that the user does not have to reach out to customer service.

BRIEF DESCRIPTION OF THE SEVERAL VIEWS OF THE DRAWINGS

The patent or application file contains at least one color drawing executed in color. Copies of this patent or patent application with color drawing(s) will be provided by the Office upon request and payment of the necessary fee.

In the drawings, which are not necessarily drawn to scale, like numerals may describe similar components in different views. To easily identify the discussion of any particular element or act, the most significant digit or digits in a reference number refer to the figure number in which that element is first introduced. Some embodiments are illustrated by way of example, and not limitation, in the figures of the accompanying drawings in which.

DETAILED DESCRIPTION

Figure 1:
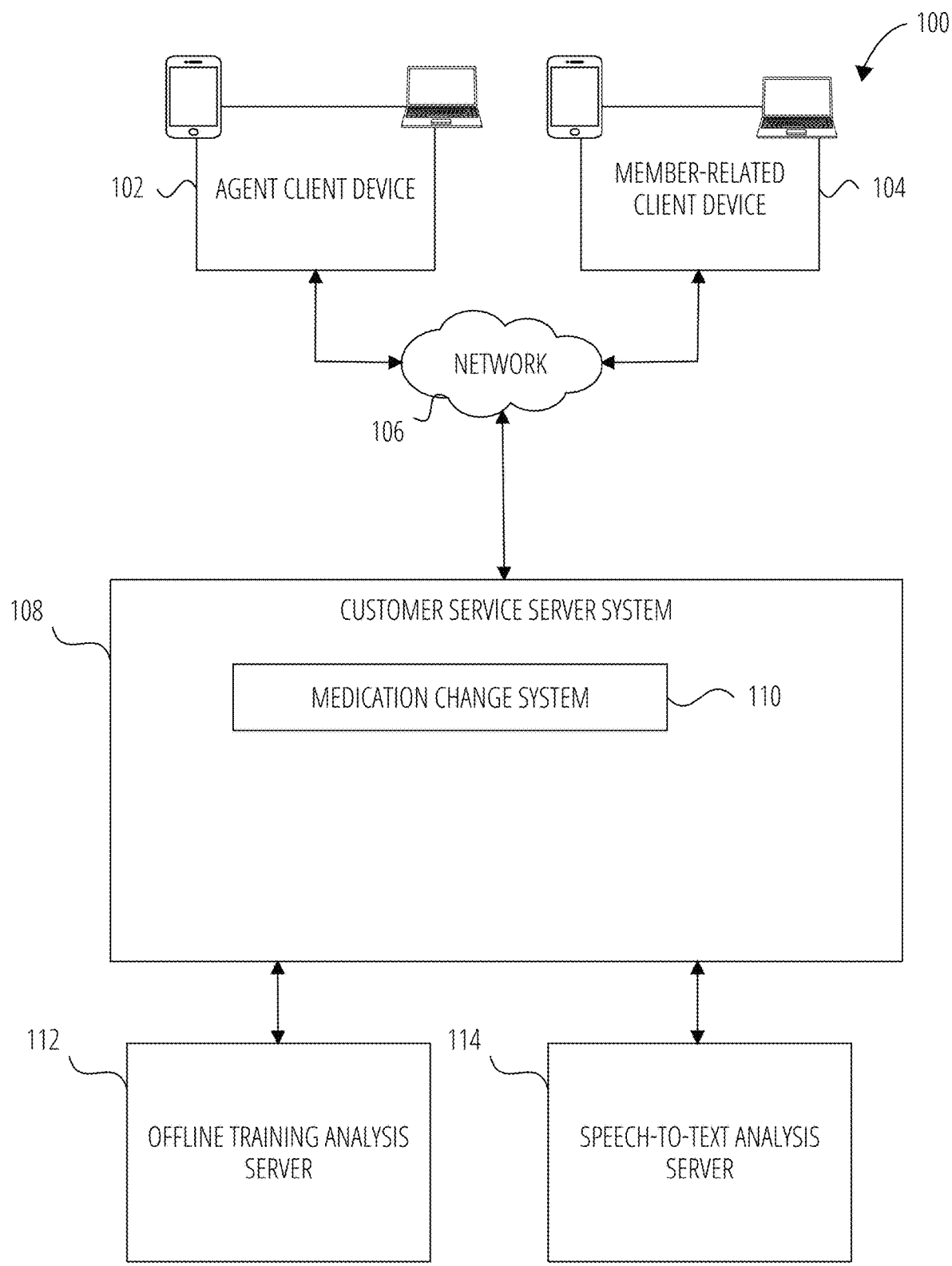
FIG. 1 is a block diagram showing an example system 100 including a medication change system 110 according to various exemplary embodiments.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Among other things, embodiments of the present disclosure improve the functionality of customer service methods and systems. In an example embodiment, the customer service can use a machine generated predictive model or artificial intelligence generated description of medications (which can be stored as entries in ordered tables). The customer service system can then use the results to provide a description of the physical characteristics of the user's medications. It is believed that this will improve not only the user experience but also adherence resulting in the possibility of improved medical outcomes. The customer service system outputs to the patient can be a description provided with a medication, e.g., on a label, with accompanying literature, inserts, and the like. The output can also be representations shown on graphical user interfaces on displays of electronic devices.

A user, e.g., a member or a representative of the member, may access the customer service of the organization. The user may contact customer service to accomplish a variety of tasks that can greatly vary in complexity. For example, simple tasks include getting assistance in registering for a username and password on the organization's website, or resetting a password associated with an online account while more complex tasks include checking an order status, placing a refill order, requesting information regarding a prescription, or requesting an explanation of benefits and terms associated with an account. Another task can be requesting data on the look and characteristics of the medication, e.g., a description of the pill, tablet, capsule, gel capsule, or the like.

To add further complexity to the servicing the user, the user can also be contacting customer service on behalf of someone else. For example, when the service provided by the organization is medical in nature, customer service call centers can receive calls or electronic messages from a user regarding prescriptions for another patient such as the user's child, spouse, parent, or charge. The user may be the member (or benefit holder). The patient (e.g., the user's child, spouse, parent, or charge) may be the member. The user can also be a professional caregiver contacting the customer service on behalf of the patient, who is the member.

A medical group may use the customer service methods and systems as described herein. A medical group may include members, people who benefit from the medical group or are provided with medical treatment by the group. The medical group can be a medical insurer. The medical group can be a pharmacy benefit manager (PBM). The PBM may store data regarding member usage of prescription drugs. This data may be leveraged in order to provide a member the prescription coverage benefit and may be paid for by a client of the PBM. The clients of the PBM can include employers, group purchasing organizations, medical health plans and governmental groups. In general, prescription drug and medicine data may be accessed from a PBM database. One or more operations may be performed on the prescription drug and medicine data to improve on the data being exchanged between a member and a user contacting the medical group system as described herein. The user contacting the medical group system can include a person related to the patient, a guardian of the patient, a caregiver of the patient, a medical care provider of the patient. In some cases, the user is also a member and is contacting the medical group on behalf of another member.

An organization can also provide its customers or members with access to customer service via different communication channels including audio calls (e.g., telephone call, VoIP, audio message, etc.) or via electronic messages (e.g., online chat, instant messaging, email, etc.). Even if the customer service experience via each of the communication channels is timely, efficient and enjoyable for the user seeking service, the user would prefer to minimize having to reach out to customer service.

Accordingly, embodiments of the present disclosure improve the functionality of the customer service methods and systems by detecting a medication change event that could cause the user to contact customer service, and by preemptively providing the user with the information regarding the medication change via a medication change interface that describes and emphasizes the differences in appearance and color of the medication in addition to the identification and details of the medications in the medication change event. The medication change can be provided to the user, who may be the patient, by printed material or by electronic means to be displayed on or audio produced on an electronic device.

Additionally, embodiments of the present disclosure improve the functionality of the customer service methods and systems by building a database of descriptors for items, such as medications, as perceived by people. The descriptors can be produced by providing images of the items to individuals over a communications system and the individuals entering inputs into the system that describe the item. These entries can be compiled in a database (e.g., fields in a table). The characteristics of the individuals can also be compiles, e.g., gender, location, age and the like and the description fields tagged to the item by an individual matching the user (e.g., a member, a customer, a patient, and the like), is used when it is helpful to include a description of the item to the member customer. This can also be used to preemptively provide the user with the information regarding the item (e.g., medication) change via an item change interface that describes and emphasizes the differences in appearance and color of the item in addition to the identification and details of the items in the item change event.

Networked Computing Environment

FIG. 1 is a block diagram showing an example system 100 according to various exemplary embodiments. The system 100 can be a customer service system that includes a customer service server system 108, an agent client device 102, and a member-related client device 104 that are communicatively coupled over a network 106 (e.g., Internet, telephony network, electronic communication network or the like). The customer service server system 108, the agent client device 102, and the member-related client device 104 can be implemented as machines 1100, as described in FIG. 11.

The agent client device 102 and the member-related client device 104 can be communicatively coupled via an audio call (e.g., VoIP, Public Switched Telephone Network, cellular communication network, etc.) or via electronic messages (e.g., online chat, instant messaging, text messaging, email, and the like). In another embodiment, the agent client device 102 and the member-related client device 104 are communicatively coupled via a voice call, e.g., using a telephony network 106. While FIG. 1 illustrates a single agent client device 102 and a single member-related client device 104, it is understood that a plurality of agent client devices 102 and a plurality of member-related client devices 104 can be included in the system 100 in other embodiments. As used herein, the term "client device" may refer to any machine that interfaces to a communications network (such as network 106) to obtain resources from one or more server systems or other client devices. A client device may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a user may use to access a network. These devices include a processor for executing instructions stored in memory that result in these devices being dedicated to the present functionality when executing the instructions. The member-related client device 104 can include a microphone and speaker on a mobile electronic device, a telephone, or a self-service kiosk, e.g., at a pharmacy, a clinic, a doctor's office, a mobile relief center, and the like. The member-related client device 104 can also include telecommunications devices for the deaf (TDD).

The network 106 may include, or operate in conjunction with, an ad hoc network, an intranet, an extranet, a virtual private network (VPN), a local area network (LAN), a wireless network, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, Gobi™, Bluetooth™, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

In the example shown in FIG. 1, a user using the member-related client device 104 can establish a communication session with an agent associated with the agent client device 102. The agent can be a human agent or an automated agent, e.g., on behalf of an organization. The automated agent can be associated with a medical group that includes the member. The automated agent can be an interactive voice response (IVR), a virtual online assistant, or a chatbot.

Figure 9:
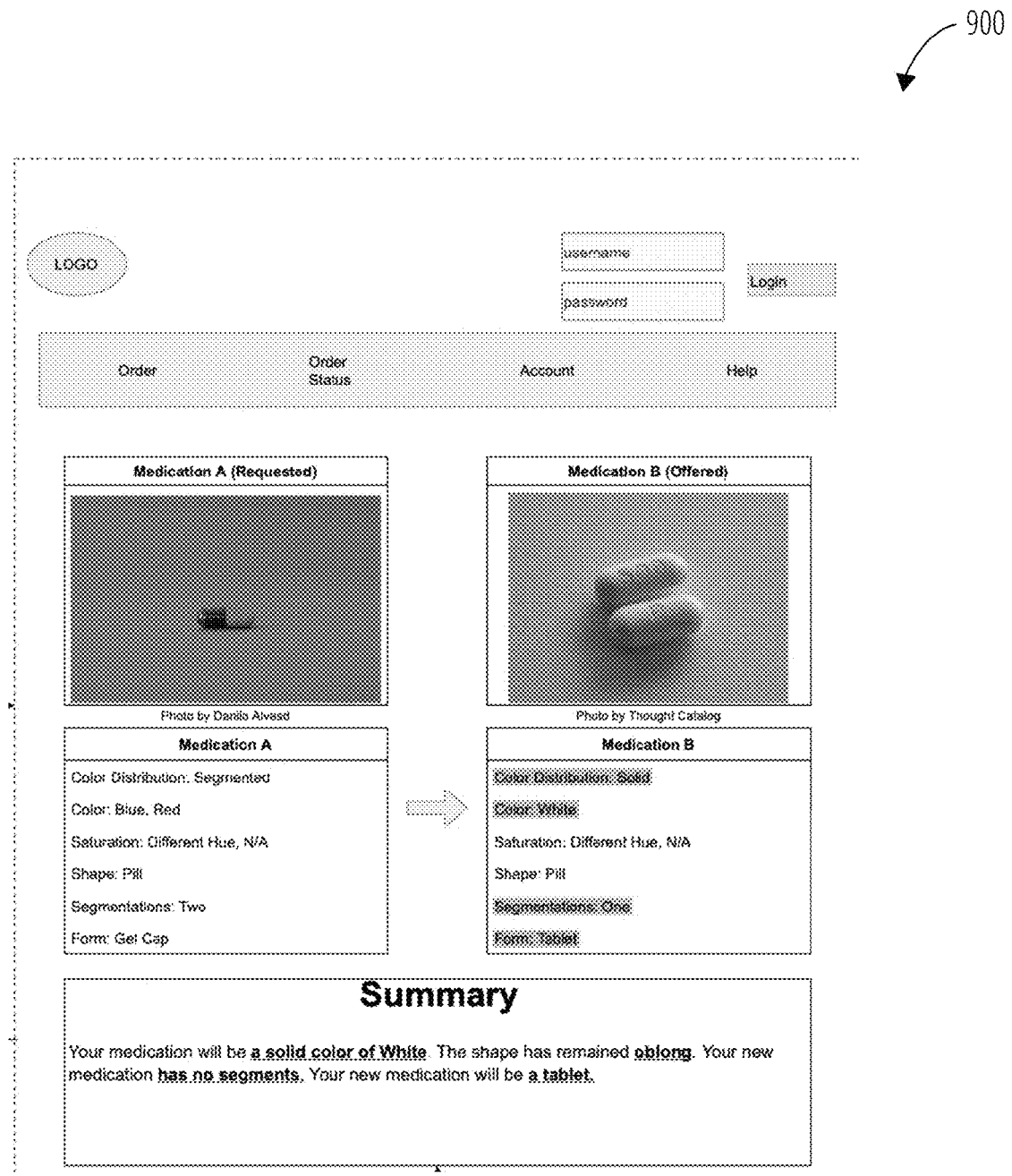
FIG. 9 is an exemplary user interface 900 of the medication change interface being displayed in operation 812 according to various aspects of the disclosure.

In another example, the user using the member-related client device 104 can access the customer service server system 108 that can cause a user interface to the organization's platform to be displayed on by the member-related client device 104 (e.g., user interface 900 in FIG. 9). In another example, the agent associated with the agent client device 102 can access the customer service server system 108 in order to train the neural networks in the customer service server system 108 which includes a medication change system 110.

Figure 10:
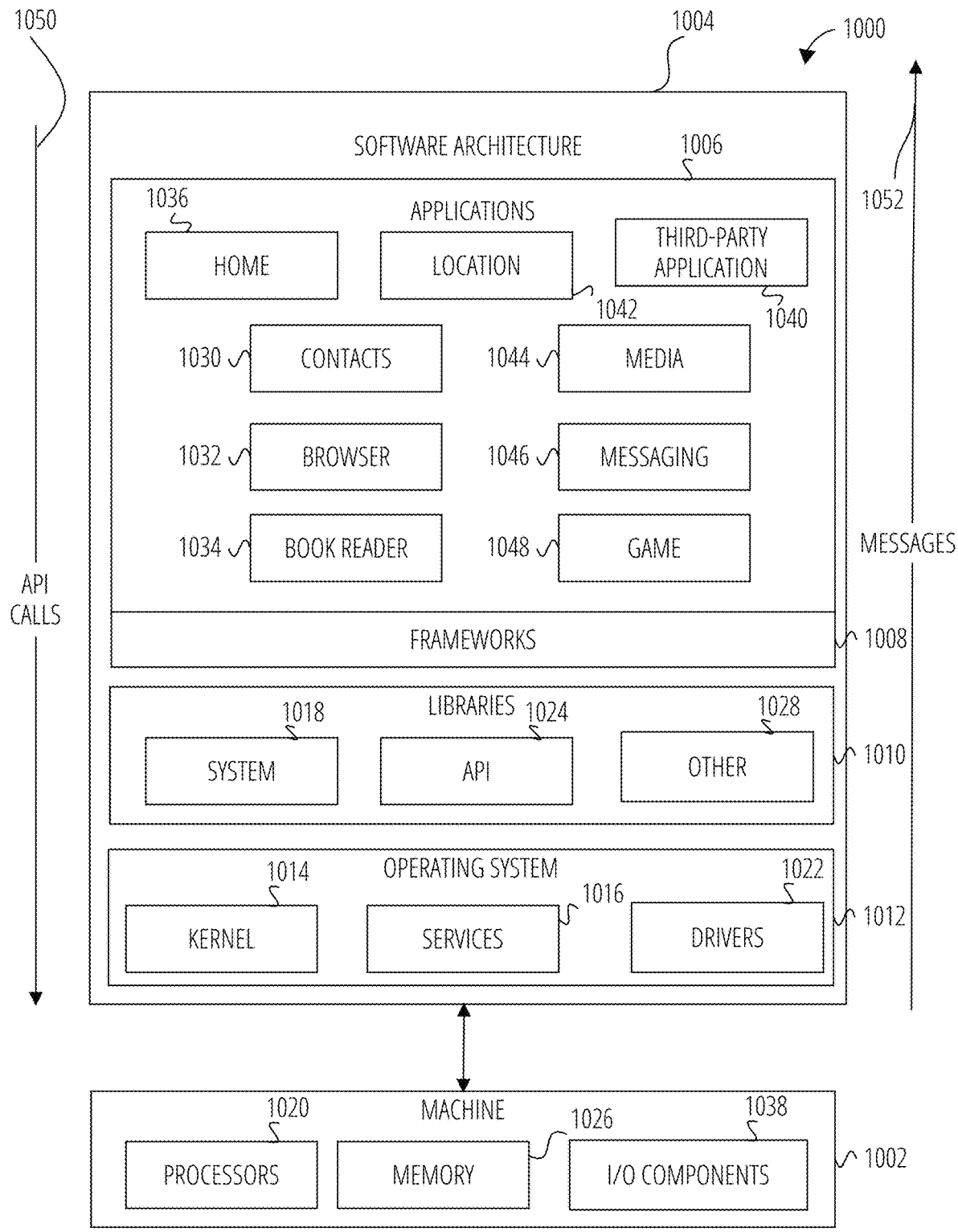
FIG. 10 is a block diagram showing a software architecture within which examples may be implemented.
Figure 11:
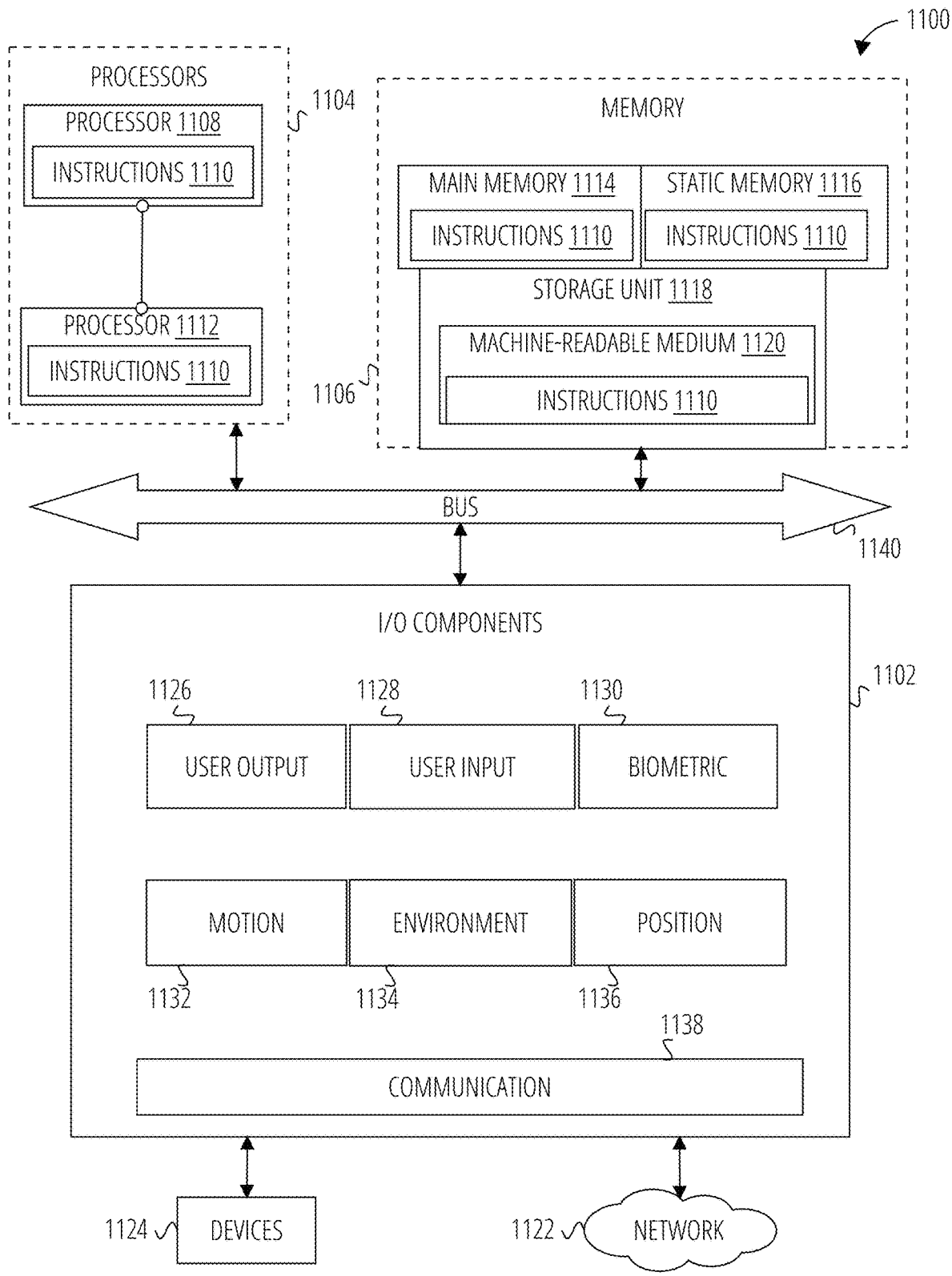
FIG. 11 is a diagrammatic representation of a machine in the form of a computer system within which a set of instructions may be executed for causing the machine to perform any one or more of the methodologies discussed herein, in accordance with some examples.

The customer service server system 108 can further include elements described with respect to FIG. 10 and FIG. 11, such as a processor and memory, having instructions stored thereon, that when executed by the processor, causes the processor to control the functions of the customer service server system 108.

As shown in FIG. 1, the system 100 can also include an offline training analysis server 112 and a speech-to-text analysis server 114 that are communicatively coupled to each other and to the customer service server system 108. In one embodiment, the offline training analysis server 112 and the speech-to-text analysis server 114 are included in the customer service server system 108 and communicatively coupled to the medication change system 110.

In one embodiment, the offline training analysis server 112 can communicate with the medication change system 110 to configure or execute the training tools for the neural networks in the medication change system 110. Examples of training tools include the captcha human perception trainer and the medication image trainer further described herein.

Medication Change System

In the customer service server system 108 of FIG. 1, the medication change system 110 detects medication change events and generates a medication change interface that notifies the user of changes in his regular medication as well as the differences in appearance and color, for example, between the medications the user should expect.

Figure 2:
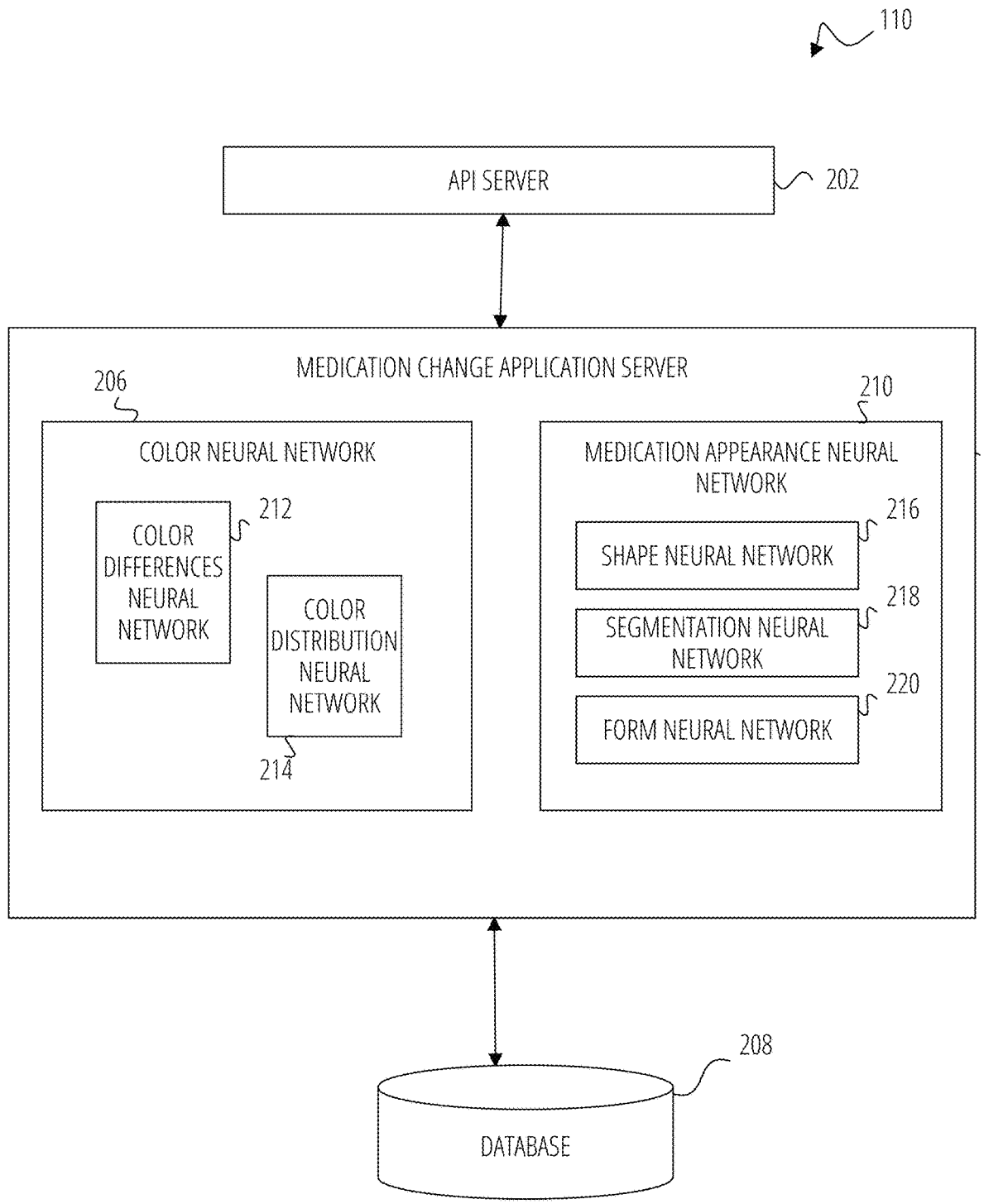
FIG. 2 is block diagram illustrating further details regarding the medication change system 110, according to exemplary embodiments.

FIG. 2 is block diagram illustrating further details regarding the medication change system 110, according to exemplary embodiments. The medication change system 110 includes an API server 202 that is coupled to and provides a programmatic interface to a medication change application server 204. For example, the medication change application server 204, using the API server 202, receive access to the details of medication change events that are detected, the medication information, and training session data to provision the neural networks in the medication change system 110, etc.

As shown in FIG. 2, the medication change application server 204 includes a color neural network 206 and a medication appearance neural network 210. The color neural network 206 can include a color differences neural network 212 that generates information on a difference in hue or saturation, a color distribution neural network 214 that generates information on a difference in color distribution, or both the color differences neural network 212 and the color distribution neural network 214. The medication appearance neural network 210 can include a shape neural network 216, a segmentation neural network 218, a form neural network 220 that generates information on a difference in shape, segmentation or (medication) form, or a combination thereof. In an example embodiment, the neural networks can include a Gated Recurrent Unit (GRU) neural network. In an example embodiment, the neural network as described herein can be a recurrent neural network (RNN). In an example embodiment, the neural network as described herein can be a convolution neural network (CNN). In an example embodiment, the neural network as described herein can include a radial basis function network.

The medication change application server 204 is communicatively coupled to the database 208, in which is stored data processed by the medication change application server 204 to generate the medication change interface, as further described herein. In one embodiment, rather than including neural networks, the medication change application server 204 includes a memory that stores instructions, when executed by a processor, causes processor to perform the operations of the medication change application server 204.

Database

Figure 3:
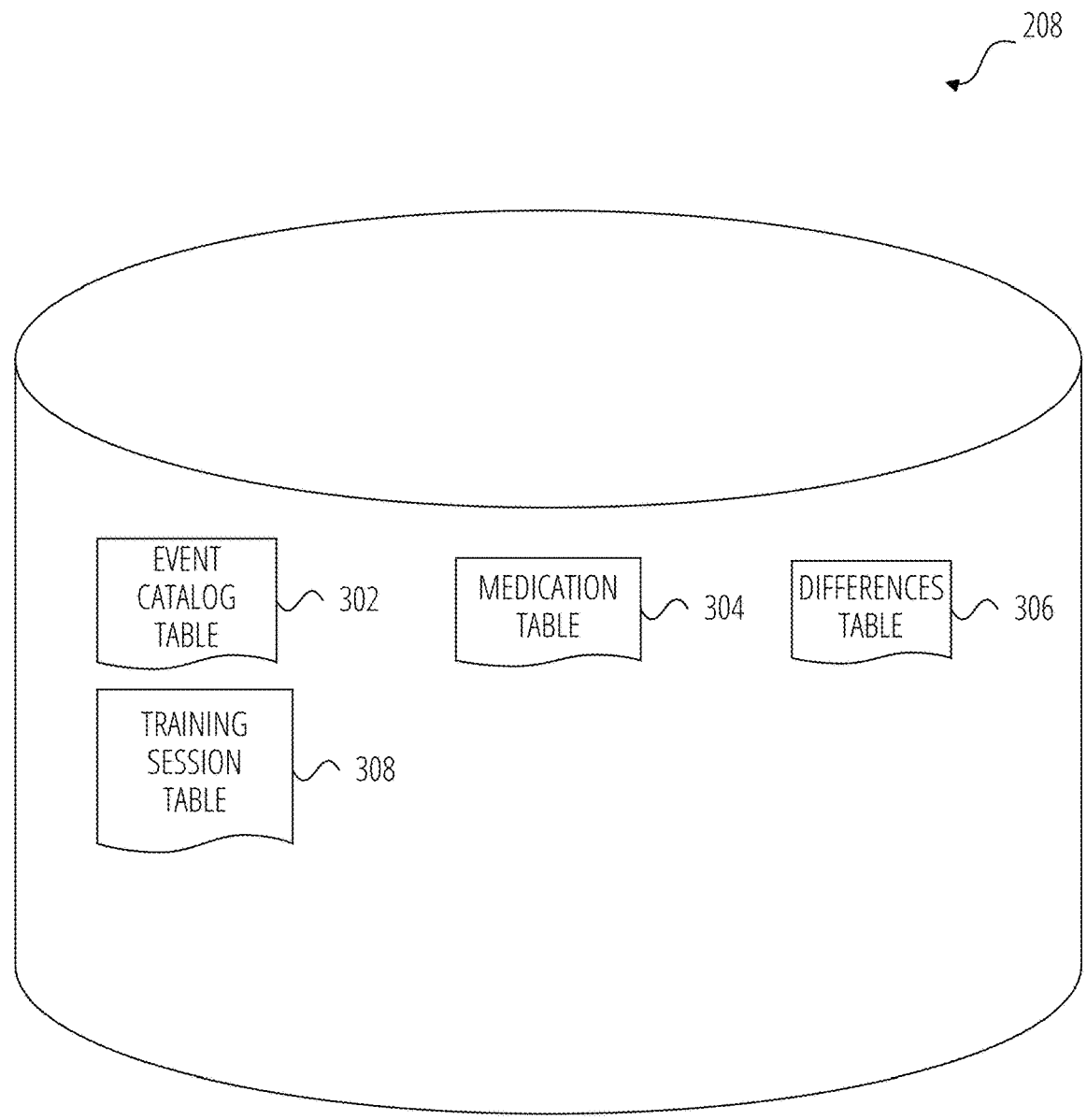
FIG. 3 is a schematic diagram illustrating data which may be stored in the database 208 of the medication change system 110, according to various exemplary embodiments.

FIG. 3 is a schematic diagram illustrating data that is stored in the database 208 of the medication change system 110, according to certain exemplary embodiments. While the content of the database 208 is shown to comprise a number of tables, the data could be stored in other types of data structures (e.g., as an object-oriented database). The database 208 includes an event catalog table 302, a medication table 304, a differences table 306, and a training session table 308. In one embodiment, the event catalog table 302, medication table 304, differences table 306, and training session table 308 are updated in real-time such that these databases comprise real-time data. In another embodiment, the tables in the database 208 updated periodically.

The event catalog table 302 can store the medication change events and the data associated with the medication change events. For example, the event catalog table 302 can store the previous medication identifier, the new medication identifier, the identification or identifier of the medical practitioner (e.g., the prescribing doctor or pharmacist), the identification or identifier of the patient, the order number, the prescription number, etc.

The medication table 304 can store, for each medication, a unique identifier, metadata, and an image of the medication. The metadata can include metadata on color distribution, color, saturation, shape, segmentation, shape, or scoring, or combinations thereof.

The differences table 306 can store a differential record for each pair of medications that comprises the image of each of the medications, the unique identifiers for each of the medications, and a differential index. The differential index can include the metadata associated with the first medication and the metadata associated with the second medication, wherein the metadata comprises metadata on color distribution, color, saturation, shape, segmentation, shape, or scoring.

The training session table 308 can store trainee responses from the color difference training using the training interface (e.g., interface 500a, interface 500b), the internal weights of the neural networks, the datasets of images for training the neural networks, etc.

Although the described flowcharts can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems, such as the systems described in FIG. 1 and/or the machine 1100 in FIG. 11.

Generating Training Dataset

Figure 4:
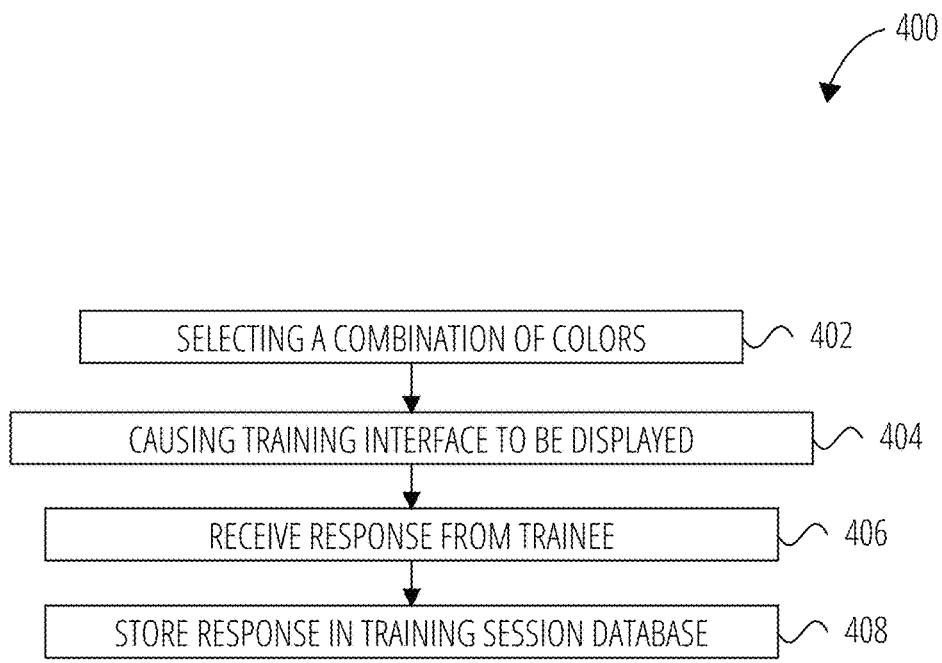
FIG. 4 is a flowchart of an exemplary process 400 of generating a training dataset for the color neural network 206 according to various aspects of the disclosure.

FIG. 4 is a flowchart of an exemplary process 400 of generating a training dataset for the color neural network 206 according to various aspects of the disclosure. The process 400 can be performed by the customer service server system 108 in FIG. 1. In one embodiment, a processor (or circuitry dedicated to performing instructed tasks) included in the customer service server system 108 performs the process 400 or causes the customer service server system 108 to perform the process 400.

Figure 5A:
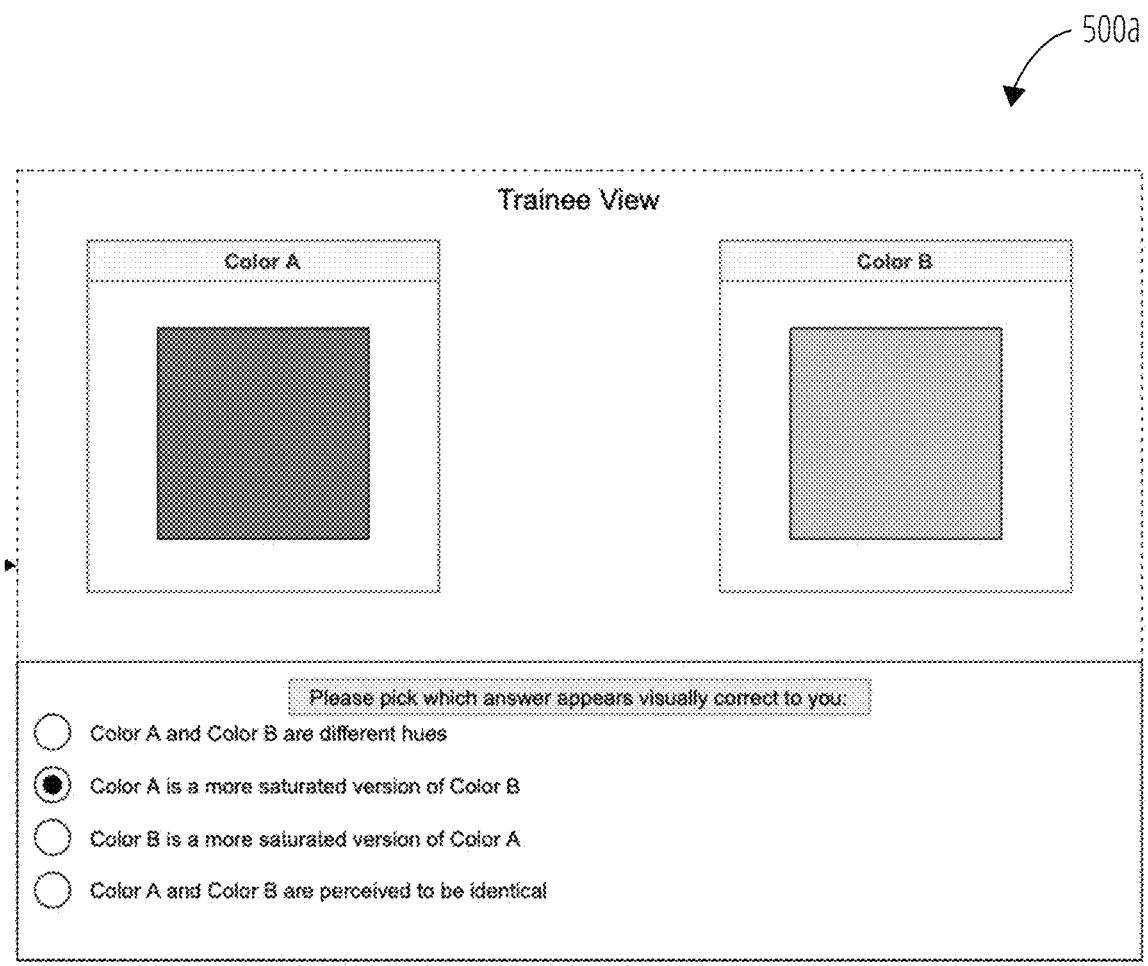
FIG. 5A is an exemplary user interface 500a of the training interface being displayed in operation 404 according to various aspects of the disclosure.
Figure 5B:
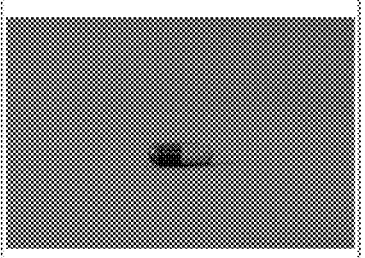
FIG. 5B is an exemplary user interface 500b of the training interface being displayed in operation 404 according to various aspects of the disclosure.

Process 400 starts, at operation 402, the processor selects a combination of colors. The system can select the colors to transmit and display on the member-related client device 104 or the agent client device 102. The colors can be based on the actual items that will be changed and need to be described to the user, e.g., a change in medication items, e.g., pills, capsules, other singulated individual dry items. At operation 404, the processor causes the training interface to be displayed on the agent client device 102 for the trainee user. In some embodiments, the processor can cause the training interface to be displayed on the member-related client device 104 for a user participating in this training of the medication change system 110. FIG. 5A and FIG. 5B are exemplary user interfaces 500a, 500b of the training interface being displayed in operation 404 according to various aspects of the disclosure.

FIG. 5A illustrates the training interface 500a for a color hue and saturation dataset and FIG. 5B illustrates a training interface 500b for a color distribution dataset. In training interface 500a, the two colors are displayed (e.g., color A and color B) and the trainee user is asked to select a response that provides information on the difference in hue or saturation. In FIG. 5A, the response choices include: "color A and color B are different hues", "color A is more saturated than color B", "color B is more saturated than color A", or "color A and color B are perceived to be identical in color".

In training interface 500b, an image of one medication is shown that comprises at least one of the colors in the combination of colors. The trainee user is asked to select a response that provides information on the difference in the color distribution. In FIG. 5B, the response choices include: "the medication is a solid color", "the medication is in multicolored segments", "the medication has multiple colors dispersed unevenly amongst each other", and "the medication is translucent".

At operation 406, the processor receives the response selected by the trainee user from the agent client device 102 and at operation 408, the processor stores the response in the training session database 208.

Training Color Neural Network

Figure 6:
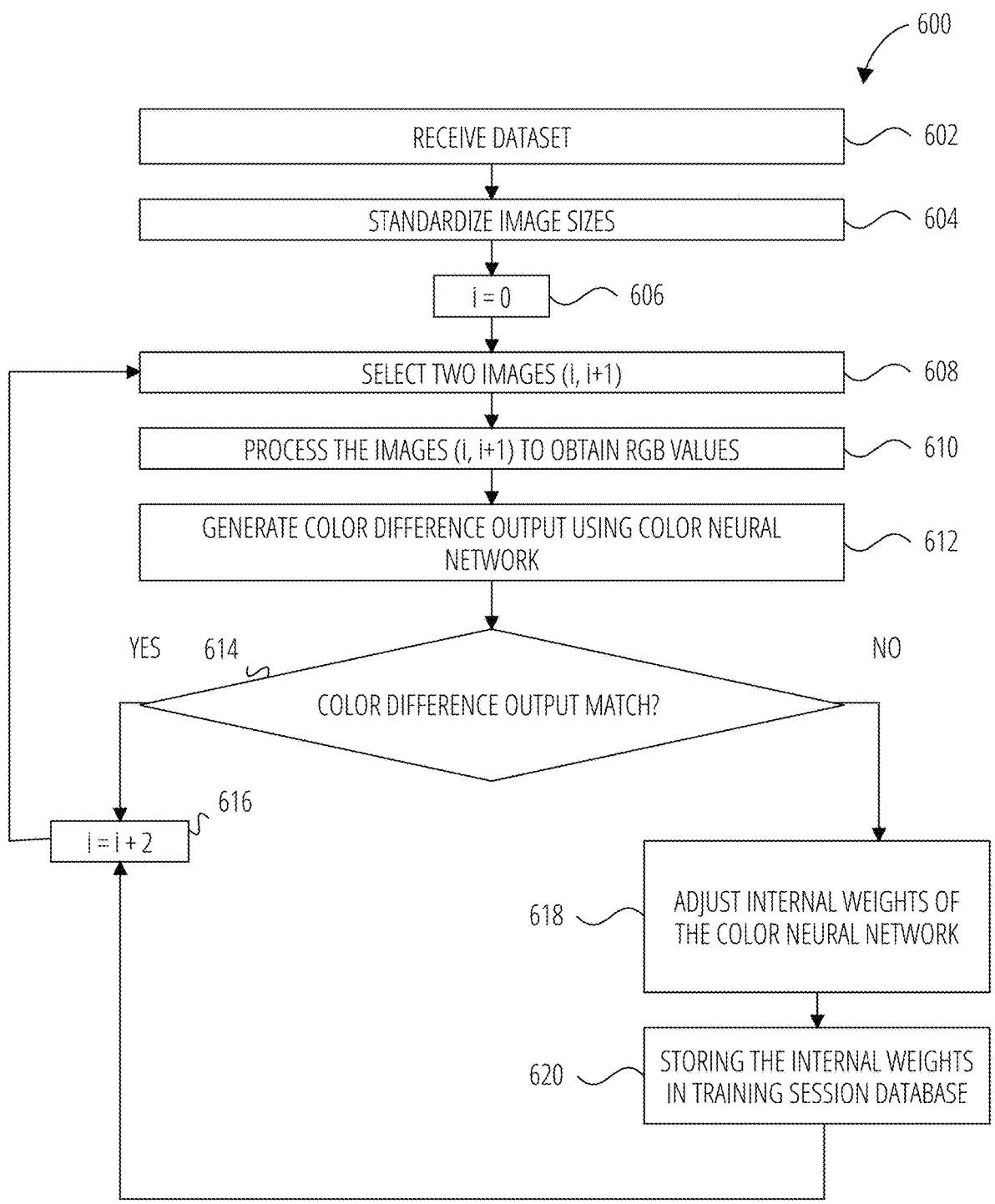
FIG. 6 is a flowchart of an exemplary process 600 of training the color neural network 206 according to various aspects of the disclosure.

FIG. 6 is a flowchart of an exemplary process 600 of training the color neural network 206 according to various aspects of the disclosure. The process 600 can be performed by the customer service server system 108 in FIG. 1. In one embodiment, a processor (or circuitry dedicated to performing instructed tasks) included in the customer service server system 108 performs the process 600 or causes the customer service server system 108 to perform the process 600.

The processor, at operation 602, receives a dataset that includes a plurality of images. At operation 604, the processor standardizes the image sizes based on the sizes of the medications depicted in the images.

At operation 606, the processor sets an index i to 0 and at operation 608, the processor selects the two images (i, i+1). In one embodiment, the processor selects images of related medications that can plausibly substituted.

At operation 610, the processor processes the images to obtain the red, green, blue (RGB) values associated with the images. For each pixel in each of the images, the processor can route the RGB value into input nodes of the color neural network.

In one example, both images' RGB values are routed into the same input layer of the color neural network. For example, for two images with n pixels, each pixel having the three Red, Green, and Blue channels respectively, there are 2*(3n) input nodes in the input layer.

The processor generates a color difference output using the color neural network, at operation 612, and determines if the color difference output matches the expected result, at operation 614. The expected result can be generated or determined by the trainer agent. The expected result can also be predetermined in the dataset. The color difference output indicates differences in hue, saturation and color distribution.

If the color difference output matches the expected result, at operation 616, the processor increases the index i by 2 and returns to operation 608 to move onto the next training pair of images. If the color difference output does not matches the expected result, at operation 618, the processor adjusts internal weights of the color neural network 206 and at operation 620, the processor stores the internal weights in the training session table 308. The processor then returns to operation 616 to increase the index i and returns to operation 608 to move onto the next training pair.

Training Medication Appearance Neural Network

Figure 7:
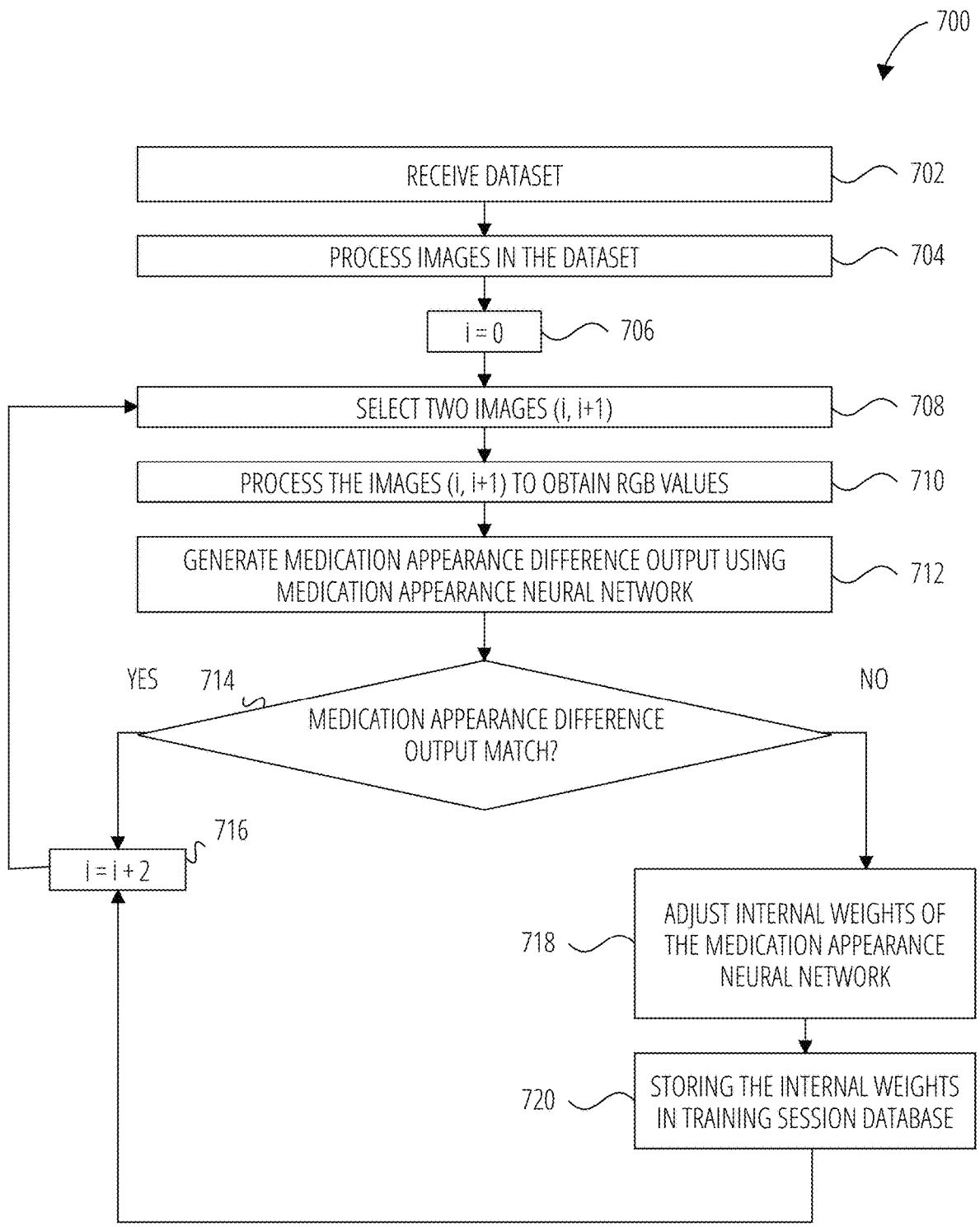
FIG. 7 is a flowchart of an exemplary process 700 of training the medication appearance neural network 210 according to various aspects of the disclosure.

FIG. 7 is a flowchart of an exemplary process 700 of training the medication appearance neural network 210 according to various aspects of the disclosure. The process 700 can be performed by the customer service server system 108 in FIG. 1. In one embodiment, a processor (or circuitry dedicated to performing instructed tasks) included in the customer service server system 108 performs the process 700 or causes the customer service server system 108 to perform the process 700.

At operation 702, the processor receives a dataset that includes images of the medication. In one embodiment, the images are collected for each medication as the medications come off the production line. For each image, a user (e.g., agent, trainer) manually tags or stores metadata pertaining to, for example, the color distribution (e.g., dispersed, segmented, solid, translucent), color (e.g., white, blue, green, etc.), saturation (e.g., low, medium, high), shapes (e.g., round, oblong, triangle, etc), segments (e.g., 1, 2, 3, etc.), medication form (e.g., capsule, tablet, injectible), scoring (e.g., single, partial, multiple, none). These tags or metadata can be compared and updated based on the captcha results from FIG. 5A, FIG. 5B, for example, to eliminate bias.

At operation 704, the processor processes the images in the dataset. For example, the processor can normalize, scale and shift the pixel values of all the images in the dataset.

At operation 706, the processor sets an index i to 0 and at operation 708, the processor selects the two images (i, i+1). In one embodiment, the processor selects images of related medications that can plausibly substituted.

For images with n×n pixels, there will be n×n input nodes per image which will result in 2(n*n) input nodes in total. (e.g., n is integer>1). These pixels are are routed into the same input layer of the color neural network.

At operation 710, the processor generates medication appearance difference output using the medication appearance neural network 210. The medication appearance difference output indicates information on the shape, segmentation and form of the medications and the differences between the medications. The medication appearance neural network 210 can include a shape neural network 216 that generates the information on the shape, a segmentation neural network 218 that generates the information on the segmentation, and a form neural network 220 that generates the information on the form.

At operation 714, the processor determines whether the medication appearance difference output matches the expected result. The expected result can be generated or determined by the trainer agent. The expected result can also be predetermined in the dataset.

If the medication appearance output matches the expected result, at operation 716, the processor increases the index i by 2 and returns to operation 708 to move onto the next training pair of images. If the color difference output does not matches the expected result, at operation 718, the processor adjusts internal weights of the medication appearance neural network 210 and at operation 720, the processor stores the internal weights in the training session table 308. The processor then returns to operation 716 to increase the index i and returns to operation 708 to move onto the next training pair.

Process of Generating a Medication Change Interface

Figure 8:
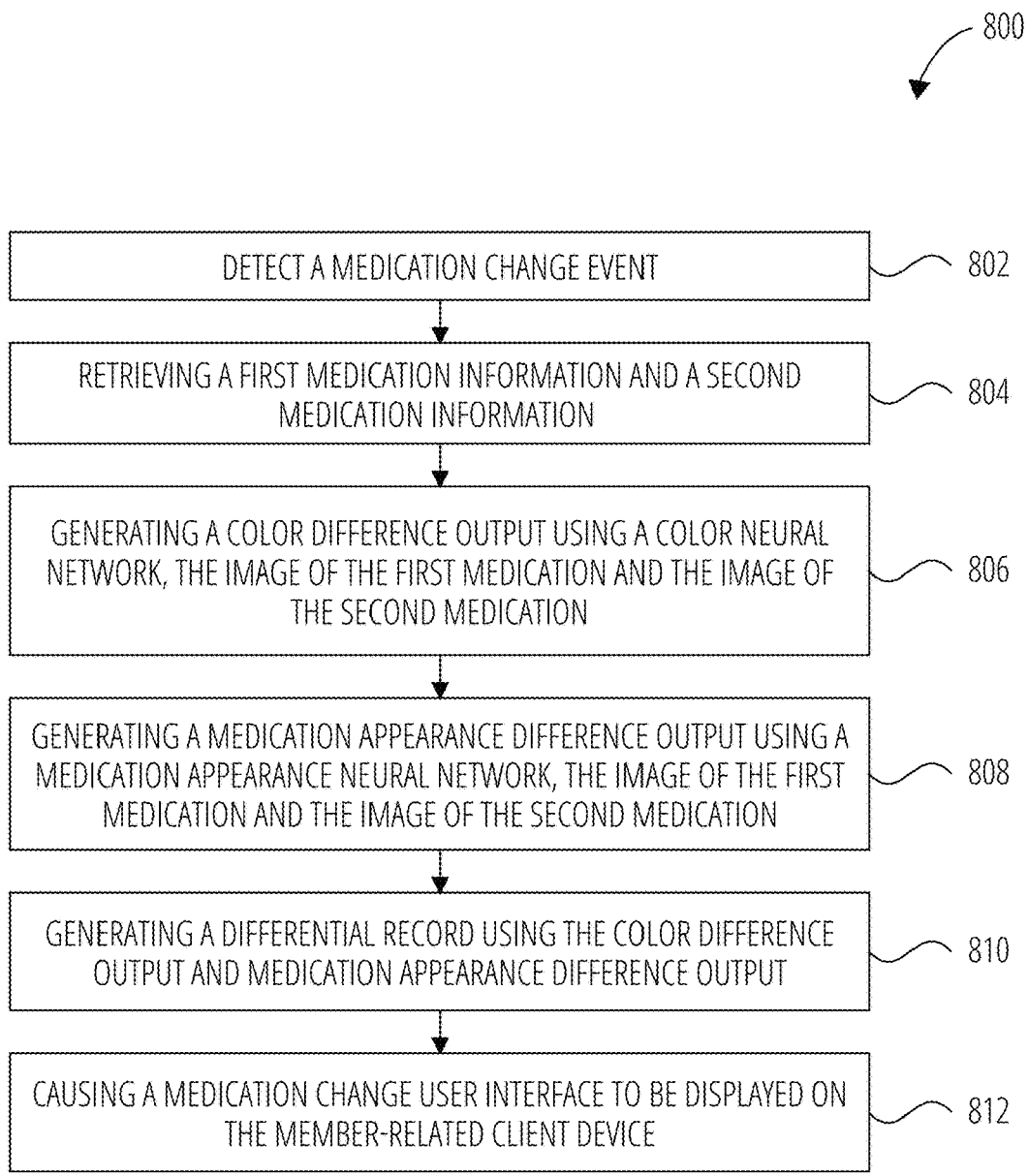
FIG. 8 is a flowchart of an exemplary process 800 of generating a medication change user interface according to various aspects of the disclosure.

FIG. 8 is a flowchart of an exemplary process 800 of generating a medication change user interface according to various aspects of the disclosure. The process 800 can be performed by the customer service server system 108 in FIG. 1. In one embodiment, a processor (or circuitry dedicated to performing instructed tasks) included in the customer service server system 108 performs the process 800 or causes the customer service server system 108 to perform the process 800.

Once each of the neural networks in the medication change system 110 is trained, the medication change system 110 can be used to generate the medication change interface (e.g., interface 900 in FIG. 9). In operation 802, the processor detects a medication change event from a member-related client device or an agent client device. Examples of a medication change event can include a doctor or medical practitioner requesting a change in the prescription for a patient, a formulary alternative to a medication is being substituted, etc. The medication change event can include a first medication identifier associated with a first medication, a second medication identifier associated with a second medication, an identification of a medical practitioner, an identification of a patient, an order number, or a prescription number. The processor can obtain the data in the medication change event from the provider, the patient or from internal or external databases.

At operation 804, the processor retrieves a first medication information and a second medication information based on the medication change event from the medication table 304. The first medication information comprises an image of the first medication and the second medication information comprises an image of the second medication. In one example, the first medication information further comprises a first unique identifier and a metadata associated with the first medication, and the second medication information further comprises a second unique identifier and a metadata associated with the second medication.

At operation 806, the processor generates a color difference output using a color neural network, the image of the first medication and the image of the second medication. The color difference output comprises information on a difference in hue, saturation or color distribution. The color neural network can comprise a color differences neural network that generates information on the difference in hue or saturation, and a color distribution neural network that generates information on the difference in color distribution.

At operation 808, the processor generates a medication appearance difference output using a medication appearance neural network, the image of the first medication and the image of the second medication. The medication appearance difference output comprises information on a difference in shape, segmentation or form. The medication appearance neural network comprises a shape neural network, a segmentation neural network, and a form neural network that generate information on the differences in shape, segmentation, and form.

At operation 810, the processor generates a differential record using the color difference output and medication appearance difference output. The differential record can comprise the image of the first medication and the image of the second medication, the first unique identifier, the second unique identifier, and a differential index At operation 812, the processor causes a medication change user interface to be displayed on the member-related client device. FIG. 9 is an exemplary user interface 900 of the medication change interface being displayed in operation 812 according to various aspects of the disclosure. As shown in FIG. 9, the medication change user interface 900 comprise the image of the first medication, the image of the second medication, and color and appearance descriptions of the first medication and the second medication. The color and appearance descriptions are displayed to emphasize differences identified in the differential record. The differences identified in the differential record can comprise differences between the first medication and the second medication that are displayed as being highlighted, bolded, or underlined.

Some of the presently described embodiments described changes to medication, e.g., pills, capsules and the like. The systems and methods described herein can also identify unit-of-use packaging changes. A unit-of-use container contains an entire prescription of a pharmaceutical and can therefore be sent to the patient without modifying the pharmaceutical(s) (e.g., the quantity, type, etc.) in the container and without product packaging modification (or with minimal product packaging modification) except for labeling with patient information. Unit-of-use products can include a full course of medicine to be taken by a patient, for example, an entire prescription (e.g., a thirty-day supply, a sixty-day supply, or a ninety-day supply). The unit-of-use products contain known quantities of medication in packages that are closed and sealed by, for example, the pharmaceutical manufacturer. As the unit-of-use product is prepared by the manufacturer, the exterior packaging can change to different shapes and colors (hues, saturation etc.), similar to the medications described herein. The unit-of-use packaging can change from a white box to a red box. The box can also display a different company logo or trademark if the medication is from a different manufacturer. The present system can inform the patient that the look of their medication will change. The change in the unit-of-use boxes can be determined by creating a training set or applying a training set to a change in unit-of-use packaging.

Software Architecture

FIG. 10 is a block diagram 1000 illustrating a software architecture 1004, which can be installed on any one or more of the devices described herein. The software architecture 1004 is supported by hardware such as a machine 1002 that includes processors 1020, memory 1026, and I/O components 1038. In this example, the software architecture 1004 can be conceptualized as a stack of layers, where each layer provides a particular functionality. The software architecture 1004 includes layers such as an operating system 1012, libraries 1010, frameworks 1008, and applications 1006. Operationally, the applications 1006 invoke API calls 1050 through the software stack and receive messages 1052 in response to the API calls 1050.

The operating system 1012 manages hardware resources and provides common services. The operating system 1012 includes, for example, a kernel 1014, services 1016, and drivers 1022. The kernel 1014 acts as an abstraction layer between the hardware and the other software layers. For example, the kernel 1014 provides memory management, processor management (e.g., scheduling), component management, networking, and security settings, among other functionality. The services 1016 can provide other common services for the other software layers. The drivers 1022 are responsible for controlling or interfacing with the underlying hardware. For instance, the drivers 1022 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1010 provide a common low-level infrastructure used by the applications 1006. The libraries 1010 can include system libraries 1018 (e.g., C standard library) that provide functions such as memory allocation functions, string manipulation functions, mathematic functions, and the like. In addition, the libraries 1010 can include API libraries 1024 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1010 can also include a wide variety of other libraries 1028 to provide many other APIs to the applications 1006.

The frameworks 1008 provide a common high-level infrastructure that is used by the applications 1006. For example, the frameworks 1008 provide various graphical user interface (GUI) functions, high-level resource management, and high-level location services. The frameworks 1008 can provide a broad spectrum of other APIs that can be used by the applications 1006, some of which may be specific to a particular operating system or platform.

In an example, the applications 1006 may include a home application 1036, a contacts application 1030, a browser application 1032, a book reader application 1034, a location application 1042, a media application 1044, a messaging application 1046, a game application 1048, and a broad assortment of other applications such as a third-party application 1040. The applications 1006 are programs that execute functions defined in the programs. Various programming languages can be employed to create one or more of the applications 1006, structured in a variety of manners, such as object-oriented programming languages (e.g., Objective-C, Java, or C++) or procedural programming languages (e.g., C or assembly language). In a specific example, the third-party application 1040 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 1040 can invoke the API calls 1050 provided by the operating system 1012 to facilitate functionality described herein.

Machine Architecture

FIG. 11 is a diagrammatic representation of the machine 1100 within which instructions 1110 (e.g., software, a program, an application, an applet, an app, or other executable code) for causing the machine 1100 to perform any one or more of the methodologies discussed herein may be executed. For example, the instructions 1110 may cause the machine 1100 to execute any one or more of the methods described herein. The instructions 1110 transform the general, non-programmed machine 1100 into a particular machine 1100 programmed to carry out the described and illustrated functions in the manner described. The machine 1100 may operate as a standalone device or may be coupled (e.g., networked) to other machines. In a networked deployment, the machine 1100 may operate in the capacity of a server machine or a client machine in a server-client network environment, or as a peer machine in a peer-to-peer (or distributed) network environment. The machine 1100 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 1110, sequentially or otherwise, that specify actions to be taken by the machine 1100. Further, while only a single machine 1100 is illustrated, the term "machine" shall also be taken to include a collection of machines that individually or jointly execute the instructions 1110 to perform any one or more of the methodologies discussed herein. The machine 1100, for example, may comprise the agent client device 102 or any one of a number of server devices in customer service server system 108. In some examples, the machine 1100 may also comprise both client and server systems, with certain operations of a particular method or algorithm being performed on the server-side and with certain operations of the particular method or algorithm being performed on the client-side.

The machine 1100 may include processors 1104, memory 1106, and input/output I/O components 638, which may be configured to communicate with each other via a bus 1140. In an example, the processors 1104 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1108 and a processor 1112 that execute the instructions 1110. The term "processor" is intended to include multi-core processors that may comprise two or more independent processors (sometimes referred to as "cores") that may execute instructions contemporaneously. Although FIG. 11 shows multiple processors 1104, the machine 1100 may include a single processor with a single-core, a single processor with multiple cores (e.g., a multi-core processor), multiple processors with a single core, multiple processors with multiples cores, or any combination thereof.

The memory 1106 includes a main memory 1114, a static memory 1116, and a storage unit 1118, both accessible to the processors 1104 via the bus 1140. The main memory 1106, the static memory 1116, and storage unit 1118 store the instructions 1110 embodying any one or more of the methodologies or functions described herein. The instructions 1110 may also reside, completely or partially, within the main memory 1114, within the static memory 1116, within machine-readable medium 1120 within the storage unit 1118, within at least one of the processors 1104 (e.g., within the Processor's cache memory), or any suitable combination thereof, during execution thereof by the machine 1100.

The I/O components 1102 may include a wide variety of components to receive input, provide output, produce output, transmit information, exchange information, capture measurements, and so on. The specific I/O components 1102 that are included in a particular machine will depend on the type of machine. For example, portable machines such as mobile phones may include a touch input device or other such input mechanisms, while a headless server machine will likely not include such a touch input device. It will be appreciated that the I/O components 1102 may include many other components that are not shown in FIG. 11. In various examples, the I/O components 1102 may include user output components 1126 and user input components 1128. The user output components 1126 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1128 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 1102 may include biometric components 1130, motion components 1132, environmental components 1134, or position components 1136, among a wide array of other components. For example, the biometric components 1130 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1132 include acceleration sensor components (e.g., accelerometer), gravitation sensor components, and rotation sensor components (e.g., gyroscope).

The environmental components 1134 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

The position components 1136 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1102 further include communication components 1138 operable to couple the machine 1100 to a network 1122 or devices 1124 via respective coupling or connections. For example, the communication components 1138 may include a network interface component or another suitable device to interface with the network 1122. In further examples, the communication components 1138 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1124 may be another machine or any of a wide variety of peripheral devices (e.g., a peripheral device coupled via a USB).

Moreover, the communication components 1138 may detect identifiers or include components operable to detect identifiers. For example, the communication components 1138 may include Radio Frequency Identification (RFID)

tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1138, such as location via Internet Protocol (IP) geolocation, location via Wi-Fi® signal triangulation, location via detecting an NFC beacon signal that may indicate a particular location, and so forth.

The various memories (e.g., main memory 1114, static memory 1116, and memory of the processors 1104) and storage unit 1118 may store one or more sets of instructions and data structures (e.g., software) embodying or used by any one or more of the methodologies or functions described herein. These instructions (e.g., the instructions 1110), when executed by processors 1104, cause various operations to implement the disclosed examples.

The instructions 1110 may be transmitted or received over the network 1122, using a transmission medium, via a network interface device (e.g., a network interface component included in the communication components 1138) and using any one of several well-known transfer protocols (e.g., hypertext transfer protocol (HTTP)). Similarly, the instructions 1110 may be transmitted or received using a transmission medium via a coupling (e.g., a peer-to-peer coupling) to the devices 1124.

Glossary

"Color" as used in some embodiments herein is the visual perceptual property as sensed by humans. The sensed color can be broken proportionally into categories of red, blue, yellow, etc. Color derives from the spectrum of light (distribution of light power versus wavelength) interacting in a person's eye with the spectral sensitivities of the light receptors. Color categories and physical specifications of color are also associated with objects or materials, e.g., an ingestible item, pill, capsule, tablet and the like, based on their physical properties such as light absorption, reflection, or emission spectra. Coatings on the ingestible item can also determine its color. By defining a color space colors can be identified numerically by their coordinates. This can provide an objective standard of color. The perception of color stems from the varying spectral sensitivity of different types of cone cells in the retina to different parts of the spectrum, colors may be defined and quantified by the degree to which they stimulate these cells and the training or experiences of the person. Such physical, physiological and physiological quantifications of color can vary amongst people. The systems and methods described herein can account for the subjective interpretation of color, e.g., as it relates to ingestible items, e.g., medication or food. In creating data sets to train machines using machine learning or artificial intelligence to describe colors, shapes and physical characteristics of ingestible items and the differences between the items.

"Carrier signal" refers to any tangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device. The instructions can include any part of a method or task as described herein.

"Client device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network. However, each of these devices loads an instruction into its electronic circuitry to be a dedicated machine to perform a task as part of the methods as described herein.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component"(or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors 1004 or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

The present disclosure describes various embodiments related to medication changes, e.g., related to medication items. Such embodiments are used for illustration and other uses are within the scope of the present disclosure. The change in a deliverable item to a user can be described using the systems and methods described herein. The item can be a type, e.g., over the counter medication, prescription medication, ingestible item, food, food packaging or the like. The change in the item being delivered can be described to the recipient when the order is placed or before the ordered items are delivered. This description of the change in appearance may ease any anxiety the recipient user may have about receiving a different looking item even though the item is functionally the same as the prior item.

What is claimed is:

1. A method comprising:
   determining, by a processor, a medication appearance change event from a member-related client device or an agent client device, the medication change event comprising a first medication identifier associated with a first medication and a second medication identifier associated with a second medication;
   retrieving, from a non-transitory computer-readable storage medium, a first medication information and a second medication information based on the medication change event, wherein the first medication information comprises an image of the first medication and the second medication information comprises an image of the second medication;
   generating a color difference output between the image of the first medication and the image of the second medication, using a color neural network, wherein the color difference output comprises information on a difference in hue, saturation or color distribution;
   generating a medication appearance difference output between the image of the first medication and the image of the second medication, using a medication appearance neural network, wherein the medication appearance difference output comprises information on a difference in shape, segmentation or form;
   generating a differential record between the image of the first medication and the image of the second medication, using the color difference output and medication appearance difference output; and
   causing a medication change user interface to be displayed when there is a difference between the image of the first medication and the image of the second medication, on the member-related client device or the agent client device, wherein the medication change user interface comprise the image of the first medication, the image of the second medication, and color and appearance descriptions of the first medication and the second medication, wherein the color and appearance descriptions are displayed to emphasize differences identified in the differential record.

2. The method of claim 1, wherein the differences identified in the differential record comprise differences between the first medication and the second medication that are displayed as being highlighted, bolded, or underlined.

3. The method of claim 1, wherein the medication change event further comprises an identification of a medical practitioner, an identification of a patient, an order number, or a prescription number.

4. The method of claim 1, wherein the first medication information further comprises a first unique identifier and a metadata associated with the first medication, wherein the second medication information further comprises a second unique identifier and a metadata associated with the second medication.

5. The method of claim 4, wherein the differential record comprises the image of the first medication and the image of the second medication, the first unique identifier, the second unique identifier, and a differential index.

6. The method of claim 5, wherein the differential index comprises the metadata associated with the first medication and the metadata associated with the second medication, wherein the metadata comprises metadata on color distribution, color, saturation, shape, segmentation, shape, or scoring.

7. The method of claim 1, wherein the color neural network comprises a color differences neural network that generates information on the difference in hue or saturation, and a color distribution neural network that generates information on the difference in color distribution.

8. The method of claim 7, wherein the information on the difference in hue or saturation comprises identifying that the first medication and the second medication are different hues, identifying that the first medication is more saturated than the second medication, identifying that the second medication is more saturated than the first medication, or identifying that the first medication and the second medication are perceived to be identical in color.

9. The method of claim 7, wherein the information on the difference in color distribution comprises identifying that the first medication and the second medication are a same color distribution or a different color distribution.

10. The method of claim 1, wherein the medication appearance neural network comprises a shape neural network, a segmentation neural network, and a form neural network that generate information on the differences in shape, segmentation, and form.

11. The method of claim 10, wherein the information on the differences in shape comprises identifying shapes of the first medication and the second medication, wherein the information on the differences in segmentation comprises identifying a number of distinguishable segments or sections in the first and second medications, wherein the information on the differences in form comprise an identification of medication form being tablet, gel capsule, or injectable.

12. A non-transitory computer-readable storage medium, the computer-readable storage medium including instructions that when executed by a computer, cause the computer to:
   determine a medication appearance change event from a member-related client device or an agent client device, the medication change event comprising a first medication identifier associated with a first medication and a second medication identifier associated with a second medication;
   retrieve, from a non-transitory computer-readable storage medium, a first medication information and a second medication information based on the medication change event, wherein the first medication information comprises an image of the first medication and the second medication information comprises an image of the second medication;
   generate a color difference output between the image of the first medication and the image of the second medication, using a color neural network, wherein the color difference output comprises information on a difference in hue, saturation or color distribution;

generate a medication appearance difference output between the image of the first medication and the image of the second medication, using a medication appearance neural network, wherein the medication appearance difference output comprises information on a difference in shape, segmentation or form;

generate a differential record between the image of the first medication and the image of the second medication, using the color difference output and medication appearance difference output; and cause a medication change user interface to be displayed when there is a difference between the image of the first medication and the image of the second medication, on the member-related client device or the agent client device, wherein the medication change user interface comprise the image of the first medication, the image of the second medication, and color and appearance descriptions of the first medication and the second medication, wherein the color and appearance descriptions are displayed to emphasize differences identified in the differential record.

13. The computer-readable storage medium of claim 12, wherein the differences identified in the differential record comprise differences between the first medication and the second medication that are displayed as being highlighted, bolded, or underlined.

14. The computer-readable storage medium of claim 12, wherein the medication change event further comprises an identification of a medical practitioner, an identification of a patient, an order number, or a prescription number.

15. The computer-readable storage medium of claim 12, wherein the first medication information further comprises a first unique identifier and a metadata associated with the first medication, wherein the second medication information further comprises a second unique identifier and a metadata associated with the second medication.

16. The computer-readable storage medium of claim 15, wherein the differential record comprises the image of the first medication and the image of the second medication, the first unique identifier, the second unique identifier, and a differential index.

17. The computer-readable storage medium of claim 16, wherein the differential index comprises the metadata associated with the first medication and the metadata associated with the second medication, wherein the metadata comprises metadata on color distribution, color, saturation, shape, segmentation, shape, or scoring.

18. The computer-readable storage medium of claim 12, wherein the color neural network comprises a color differences neural network that generates information on the difference in hue or saturation, and a color distribution neural network that generates information on the difference in color distribution.

19. The computer-readable storage medium of claim 12, wherein the medication appearance neural network comprises a shape neural network, a segmentation neural network, and a form neural network that generate information on the differences in shape, segmentation, and form.

20. A computing apparatus comprising:
a processor; and
a memory storing instructions that, when executed by the processor, configure the apparatus to:

determine a medication appearance change event from a member-related client device or an agent client device, the medication change event comprising a first medication identifier associated with a first medication and a second medication identifier associated with a second medication;

retrieve, from a non-transitory computer-readable storage medium, a first medication information and a second medication information based on the medication change event, wherein the first medication information comprises an image of the first medication and the second medication information comprises an image of the second medication;

generate a color difference output between the image of the first medication and the image of the second medication, using a color neural network, wherein the color difference output comprises information on a difference in hue, saturation or color distribution;

generate a medication appearance difference output between the image of the first medication and the image of the second medication, using a medication appearance neural network, wherein the medication appearance difference output comprises information on a difference in shape, segmentation or form;

generate a differential record between the image of the first medication and the image of the second medication, using the color difference output and medication appearance difference output; and cause a medication change user interface to be displayed when there is a difference between the image of the first medication and the image of the second medication, on the member-related client device or the agent client device, wherein the medication change user interface comprise the image of the first medication, the image of the second medication, and color and appearance descriptions of the first medication and the second medication, wherein the color and appearance descriptions are displayed to emphasize differences identified in the differential record.

* * * * *